United States Patent
Miettinen et al.

(10) Patent No.: US 9,967,916 B1
(45) Date of Patent: May 8, 2018

(54) SYSTEM FOR PROVIDING WRIST DEVICE WITH CELLULAR COMMUNICATION CAPABILITY

(71) Applicant: POLAR ELECTRO OY, Kempele (FI)

(72) Inventors: Jari Miettinen, Oulu (FI); Marko Tilvis, Oulunsalo (FI); Juha Sorvala, Oulu (FI); Harri Määttä, Kempele (FI); Vesna Somero, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 0 days. days.

(21) Appl. No.: 15/661,807

(22) Filed: Jul. 27, 2017

(30) Foreign Application Priority Data

Dec. 9, 2016 (GB) .................................. 1621010.6

(51) Int. Cl.
| | | |
|---|---|---|
| H04W 72/00 | (2009.01) |
| H04W 76/02 | (2009.01) |
| H04W 72/04 | (2009.01) |
| H04B 1/3827 | (2015.01) |
| H04W 84/18 | (2009.01) |
| H04W 84/04 | (2009.01) |
| H04W 88/02 | (2009.01) |

(52) U.S. Cl.
CPC ............ H04W 76/10 (2018.02); H04B 1/385 (2013.01); H04W 72/04 (2013.01); H04W 76/02 (2013.01); *H04W 84/042* (2013.01); *H04W 84/18* (2013.01); *H04W 88/02* (2013.01)

(58) Field of Classification Search
CPC .... A61B 2560/0242; A61B 2560/0431; A61B 2560/0456; A61B 5/0002; A61B 5/1112; A61B 5/1113; A61B 5/0022; A61B 5/0205; A61B 5/021; A61B 5/02438; A61B 5/11; A61B 5/681; A61B 5/6898; A61B 5/742; H04W 76/10
USPC ..... 455/41.2, 404.2, 404.1, 410, 418, 456.6, 455/556.1, 566, 450
See application file for complete search history.

(56) References Cited

U.S. PATENT DOCUMENTS

| | | | |
|---|---|---|---|
| 2011/0103329 A1* | 5/2011 | Baek | H04W 28/065 370/329 |
| 2016/0034696 A1* | 2/2016 | Jooste | G06F 1/163 726/1 |
| 2017/0172424 A1* | 6/2017 | Eggers | A61B 5/0205 |
| 2017/0280412 A1* | 9/2017 | Chen | H04W 64/00 |

FOREIGN PATENT DOCUMENTS

| | | |
|---|---|---|
| JP | 2010-220036 | 9/2010 |
| WO | 2012083512 A1 | 6/2012 |
| WO | 2013035058 A1 | 3/2013 |

* cited by examiner

*Primary Examiner* — Fred Casca
(74) *Attorney, Agent, or Firm* — Hoffmann & Baron, LLP (57) ABSTRACT

A method for operating cellular connectivity in a wearable device includes configuring a sensor device to measure physical activity of a user and to output measurement data representing the measured physical activity; establishing, by using a cellular radio device included in the wearable device, cellular connectivity with an access node of a cellular communication system; and adjusting utilization of cellular uplink resources allocated to the cellular radio device according to a rate at which the measurement data from the sensor device becomes available for uplink transmission in the wearable device.

19 Claims, 6 Drawing Sheets

SYSTEM FOR PROVIDING WRIST DEVICE WITH CELLULAR COMMUNICATION CAPABILITY

CROSS-REFERENCE TO RELATED APPLICATION

This application claims benefit to Application No. GB 1621010.6, filed Dec. 9, 2016, which is incorporated by reference herein in its entirety.

BACKGROUND

Field

The invention relates to physical activity monitoring devices provided with a cellular modem and to a system for utilizing this capability.

Description of the Related Art

With the development of cellular communication protocols towards better support for low power consumption, it has become possible to provide a cellular modem in small devices with very limited power resources. With the development of Internet of Things and machine-type communications, new services are being built on top of this feature. Wearable physical activity monitoring devices may also benefit from this aspect, and new technical functions may be designed for such devices to employ the services provided by cellular connectivity.

SUMMARY

The invention is defined by the subject-matter of the independent claims. Embodiments are defined in the dependent claims.

BRIEF DESCRIPTION OF DRAWINGS

In the following, the invention will be described in greater detail with reference to the embodiments and the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Embodiments described in this document may be implemented in a radio system, such as in at least one of the following: Universal Mobile Telecommunication System (UMTS, 3G) based on basic wideband-code division multiple access (W-CDMA), high-speed packet access (HSPA), Long Term Evolution (LTE), LTE-Advanced, 5G system, and/or a future system.

The embodiments are not, however, restricted to the system given as an example but a person skilled in the art may apply the solution to other communication systems provided with necessary properties. One example of a suitable communications system is the 5G system, as listed above. 5G has been envisaged to use multiple-input-multiple-output (MIMO) multi-antenna transmission techniques, a higher number of base stations or nodes than the current network deployments of LTE, e.g. by employing a so-called small cell concept, including macro sites operating in co-operation with smaller local area access nodes. 5G may employ more than one radio access technology (RAT), each RAT optimized for certain use cases and/or spectrum. 5G mobile communications will have a wider range of use cases and related applications including video streaming, augmented reality, different ways of data sharing and various forms of machine type applications, vehicular safety, different sensors implementations and real-time control. 5G is expected to cooperate with existing legacy radio access technologies, such as the LTE. Integration with the LTE may be implemented, at least in the early phase, as a system, where macro coverage is provided by the LTE and 5G radio interface access comes from small cells by aggregation to the LTE. In other words, 5G is planned to support both inter-RAT operability (such as LTE-5G).

Figure 1:
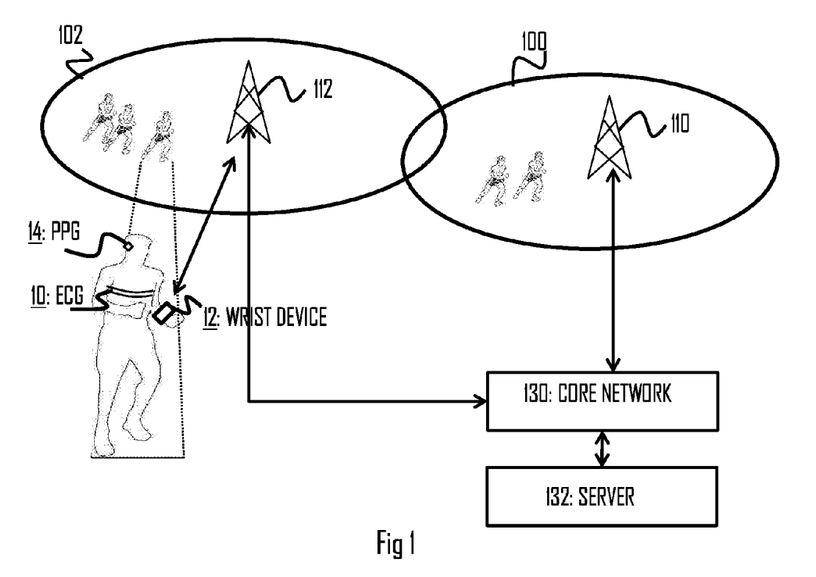
FIG. 1 illustrates a wireless communication scenario to which embodiments of the invention may be applied.

FIG. 1 illustrates an example of a communication system to which some embodiments of the invention may be applied. The system may comprise at least one access node 110, 112 providing and managing a cell 100, 102. The cell may be, e.g., a macro cell, a micro cell, femto, or a pico cell, for example. From another point of view, the cell may define a coverage area or a service area of the access node 110, 112. The access node 110, 112 may be an evolved Node B (eNB) as in the LTE and LTE-A, or any other apparatus capable of controlling radio communication and managing radio resources within a cell. For 5G solutions, the implementation may be similar to LTE-A, as described above. The access node 110, 112 may be called a base station or a network node. The system may be a cellular communication system composed of a radio access network of access nodes, each controlling a respective cell or cells. The access nodes may provide terminal devices 12 with wireless access to other networks such as the Internet. In some scenarios, one or more local area access nodes may be arranged within a control area of a macro cell access node. The local area access node may provide wireless access within a sub-cell that may be comprised within a macro cell. Examples of the sub-cell may include a micro, pi-co and/or femto cell. Typically, the sub-cell provides a hot spot within the macro cell. The operation of the local area access node may be controlled by an access node under whose control area the sub-cell is provided.

The access nodes may be connected via an interface to a core network 130 of the cellular communication system. The LTE specifications specify the core network as an evolved packet core (EPC), and the core network may comprise at least a mobility management module (MME) and a gateway (GW) node. The MME may handle mobility of terminal devices in a tracking area encompassing a plurality of cells and also handle signalling connections between the terminal devices and the core network 130, authentication of the terminal devices, etc. The gateway node may handle data routing in the core network 130 and to/from the terminal devices.

The 5G system is designed to provide improved power-saving features and reduced latencies for data transmission. These features make the cellular connectivity suitable for new types of services. For example, with the 5G capability, a cellular radio device may be implemented in wearable devices having smaller battery resources, such as wrist devices 12. A wrist device 12 may be a smart watch provided with sensor functions to measure one or more physical states of a user. The wrist device 12 may be considered as a training computer capable of acquiring, processing, and transmitting wirelessly physical activity data measured by one or more physical or physiological sensors.

At least some of the sensors may be wearable sensor devices. The sensors may employ one or more measurement technologies for measuring heart activity of a user. Other sensor may comprise inertial sensors configured to measure motion of the user or a certain bodily part of the user, e.g. arm, torso, head, or foot. An inertial sensor may include at least one of an accelerometer (or multiple accelerometers such as a three-dimensional accelerometer), a gyroscope, and a magnetometer. A sensor device 10 may be configured to measure electrocardiogram (ECG) of the 20. Such an ECG sensor 10 may comprise one or more electrodes arranged to be in contact with the user's skin in order to measure electric charges generated during each heartbeat. The ECG sensor may be portable to enable the measurement during an outdoors physical exercise, such as running or cycling.

At least one sensor device 12, 14 may be configured to measure a photoplethysmogram (PPG) optically. PPG represents a volumetric measurement of an organ. A PPG sensor 12, 14 may comprise a light source such as a light emitting diode (LED) configured to illuminate a skin of the user and, further, comprise a light-sensitive sensor such as a photodiode configured to measure changes in light reflected from the illuminated skin. With each cardiac cycle, the heart pumps blood to peripheral arteries. Even though this blood wave pulse is damped by the artery system as it propagates, it is enough to distend arteries and arterioles in the subcutaneous tissue. If the light source and the light-sensitive sensor are place appropriately against the skin, the blood wave pulse can be detected as a change in the reflecting light measured by using the light-sensitive sensor. Each cardiac cycle appears as a peak in a measurement signal acquired through the light-sensitive sensor. The blood pulse wave may be modulated by multiple other physiological systems and, therefore, the PPG may also be used to monitor breathing, hypovolemia, and other physiological conditions. The PPG may be measured at various locations of the human body, e.g. from a wrist (PPG sensor in the wrist device 12), head, ear canal or ear leaf (sensor 14).

Some sensor devices may be configured to be attached to an exercise machine or apparatus used by the user during a physical exercise. Such an apparatus may be a bicycle or a gym device, for example. Such a sensor device may include a power sensor configured to measure mechanical power or a cycling cadence sensor, for example.

Since the wrist device 12, or another wearable device, is provided with the cellular radio device comprising a cellular radio modem operating according to the specifications of the 5G system or another cellular communication system, the wrist device 12 is capable of communicating bidirectionally with the access nodes 110, 112. The wrist device may utilize this cellular connectivity to communicate with a server computer 132 connected to the cellular communication system and the access nodes 110, 112 via Internet, for example. The server computer 132 may be configured to provide the wrist device 12 with a physical activity service, e.g. one of the services described below. The server computer 132 may employ the access nodes 110, 112 to transmit, broadcast, and/or multicast messages to the wearable devices 12 of the users registered to the physical activity service. The wearable devices 12 may employ the access nodes to upload measurement data for processing at the server computer 132. Latest cellular communication systems such as the 5G system provides very low latencies, e.g. in the order of milliseconds, which enables provision of new services. Some of such services are described below.

Figure 2:
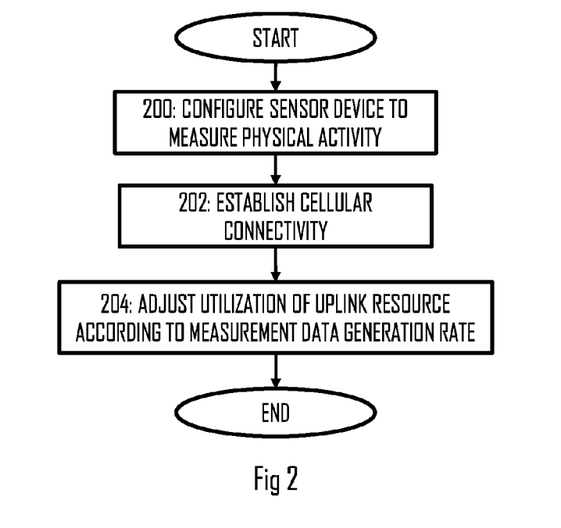
FIG. 2 illustrates a process for adjusting utilization of wireless uplink resources according to an embodiment of the invention.

The cellular communication systems providing terminal devices such as the wearable device 12 with cellular connectivity allocate uplink communication resources to the terminal devices for uplink transmission of data. With the very low latency, the data may be transmitted by the terminal devices with better real-time characteristics. FIG. 2 illustrates an embodiment of a process for adapting the cellular connectivity to the measurement operation of the sensor devices 10 to 14. The process may be carried out in the wearable device comprising a cellular radio device, e.g. a radio modem operating according to a cellular communication protocol. Referring to FIG. 2, let us describe a method for operating cellular connectivity in the wearable device, the method comprising: configuring (block 200) a sensor device to measure physical activity of a user and to output measurement data representing the measured physical activity; establishing (block 202), by using a cellular radio device comprised in the wearable device, cellular connectivity with an access node of a cellular communication system; and adjusting (204) utilization of cellular uplink resources allocated to the cellular radio device according to a rate at which said measurement data from the sensor device becomes available for uplink transmission in the wearable device.

Matching the utilization of the cellular uplink resources with the rate at which the measurement data becomes available for uplink transmission, e.g. at an uplink buffer of the cellular radio device, provides the advantage that the uplink data may be transmitted with lower delay which improves the latency at which the measurement data is delivered to the server computer 132.

Figure 3:
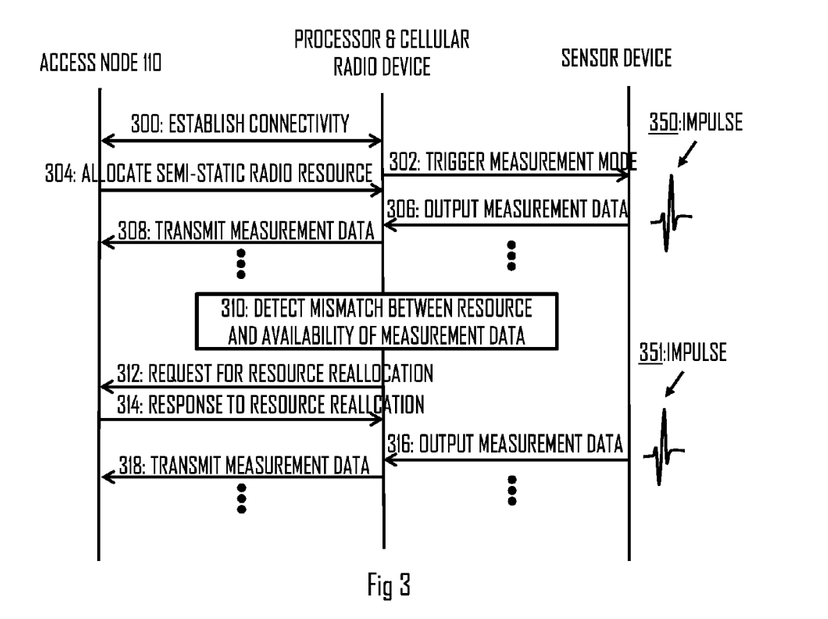
FIG. 3 illustrates a signaling diagram of an embodiment of FIG. 2.

Let us now describe an embodiment of the process of FIG. 2 with reference to a signalling diagram of FIG. 3. FIG. 3 illustrates signalling between a sensor device, a processor and the cellular radio device of the wearable device, and an access node 110 of the cellular communication system. In an embodiment, the sensor device is in the wearable device, e.g. in the same housing with the processor and the cellular radio device. In another embodiment, the sensor device is external to the wearable device, and the wearable device and the sensor device communicate over a wireless connection established according to a wireless communication protocol such as Bluetooth®, Bluetooth Smart®, another short-range radio communication protocol, or an induction-based communication scheme.

Referring to FIG. 3, the processor configures the cellular radio device to establish the cellular connectivity with a radio access network of the cellular communication system through the access node 110 in step 300. Step 300 may comprise establishing one or more bearer services for the cellular radio device in the cellular communication system. The access node 110 and, in some embodiments, other elements of the cellular communication system may perform functions such as admission control and authentication of the cellular radio device in step 300. Step 300 may comprise establishment of communication parameters for a radio connection and a core network connection for the cellular radio device according to a protocol of the cellular communication system. Upon establishing the cellular connectivity, e.g. establishing the radio access connection, the access node may allocate an uplink radio resource to the cellular radio device (Step 304). The radio resource may be allocated in a semi-static manner such that an uplink time-frequency resource is allocated to the cellular radio device in a repetitive manner. A periodicity may be associated with the allocation such that the time-frequency resource is reserved for the cellular radio device in a periodic manner.

Upon establishing the cellular connectivity in step 300, or before step 300, the processor may configure the sensor device to start a measurement mode in which the sensor device performs measurements it is configured to perform, e.g. heart activity measurements, and output measurement data to the processor 306. In an embodiment, triggering step 302 in response to a user input, for example, triggers also step 300. In an embodiment, the sensor device is configured to output the measurement data in step 306 upon detecting a certain event in the measurement data or upon processing the measurement data to a certain degree. An embodiment of the certain event is detection of an event in a measurement signal, e.g. a peak. An embodiment of the processing the measurement data to the certain degree is computation of energy expenditure from the measurement data.

The measurement data may be received by the processor in step 306. Upon detecting the reception of the measurement data from the sensor device, the processor may output the measurement data to a buffer of the cellular radio device, and the cellular radio device may be configured to transmit the measurement data in the next available uplink resource in step 308. In this manner, the process may proceed and the measurement data may be streamed to the server computer 132 as it becomes available for transmission.

The processor and/or the cellular radio device may be configured to monitor the status of the uplink buffer and attempt to keep the buffer as empty as possible. This may be realized by scaling the amount of uplink resources such that the amount of radio resource matches with or is greater than the rate and amount of measurement data appearing in the buffer. In greater detail, the status of the uplink buffer may be compared with the allocated uplink resources and, upon detecting a mismatch between the available uplink resources and the rate at which the sensor device outputs measurement data for uplink transmission in block 310, the processor may configure the cellular radio device to request for resource reallocation in step 312.

In an embodiment, the mismatch is the lack of sufficient uplink resources that results in the uplink buffer filling with uplink data and causing delay to the uplink transmission. In this case, the request in step 312 may indicate a need for additional uplink resources.

In an embodiment, the mismatch is excess of uplink resources. In such a case, the request in step 312 may indicate release of at least some of the allocated radio resources.

Upon receiving the request, the access node may process the request, determine whether or not the request can be admitted and the uplink resources reallocated in the requested manner. Upon determining that the resource reallocation is possible, the access node may respond to the request of step 312 with a response message in step 314, wherein the response message indicates new uplink resources for the cellular radio device. Thereafter, the processor and the cellular radio device may carry out reception of the measurement data form the sensor device (step 316) and transmit the measurement data in the reallocated uplink resources (step 318). In this manner, the processor and the cellular radio device may continuously evaluate whether or not the currently allocated uplink resources match with the rate at which the sensor device outputs the measurement data and attempt to minimize the time the measurement data is stored in the uplink buffer.

In an embodiment, the low latency of the modern cellular communication system and the procedure of FIG. 3 is utilized to stream heart activity measurement data as it becomes available. For example, an indication of a heart beat impulse 350, 351 may be transmitted as soon as the impulse 350, 351 is detected by the sensor device. Conventionally, such a procedure has been employed between a heart rate transmitter such as one attached to the user's chest and a training computer such as a wrist computer. When the latency of uplink transmissions between the wearable device 12 and the server computer 132 is in the order of milliseconds, this scheme may be expanded to the communication between the training computer (the wearable device) and the server computer 132. Upon detecting the impulse 350, 351 in the form of a peak in the ECG or PPG measurement data, the sensor device may output in step 306, 316 an indication of the detected impulse. As a response, the processor may configure the cellular radio device to transmit uplink data indicating the detection of the heart beat impulse to the server computer. In this manner, at least some of the processing of the heart activity measurement data may be outsourced to the server computer. The server computer may compute, for example, energy expenditure, heart rate or, provided that the latency is low, heart rate variability (HRV) used in estimation of training load, for example. Similar approach may be applied to other types of measurement data, e.g. motion measurement data acquired from one or more motion sensors.

Figure 4:
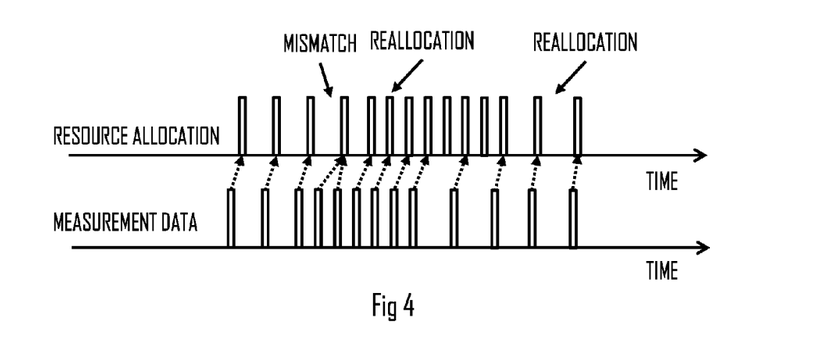
FIG. 4 illustrates adaptation of uplink resources to a rate of measurement data generation in a wearable device.

FIG. 4 illustrates a timing diagram illustrating the rate at which the measurement data becomes available (a timeline referred to as "Measurement Data") and timing of the resource allocations of the cellular radio device (a timeline referred to as "Resource Allocation"). The reader may assume that the timelines are aligned to the same time. As illustrated in FIG. 4, the measurement data is at first transmitted as it becomes available for uplink transmission. The measurement data is transmitted in the next uplink resource that follows the measurement data appearing in the uplink buffer of the cellular radio device. In this situation, the uplink resources are well aligned with the rate at which the measurement data becomes available and the measurement data may be transmitted without significant delay caused by buffering. Then, the rate at which the measurement data becomes available changes such that the rate is increased. This may result in a mismatch between the allocated resources and the rate which results in that multiple instances of the measurement data are bundled and transmitted in the same uplink resource. If the uplink resource is great enough to deliver all the measurement data, the mismatch may still be acceptable. However, in a case where measurement data has to wait in the buffer over one or more uplink transmission occasions, the mismatch may become unacceptable because of high latency. As a consequence, the processor may configure the cellular radio device to request for more uplink resource (step 312). The request may also specify the requested resource in greater detail, e.g. by defining the amount of resources per allocation, timing of the uplink resources, etc. After the reallocation, the uplink resources may again be aligned with the rate at which the measurement data becomes available.

In the event where the rate at which the measurement data becomes available reduces, e.g. the user's heart rate drops because of more relaxed period in the exercise, there may again be a mismatch between the rate and the amount of allocated resource. In this event, since the measurement data becomes available with lower rate, there may be one or more uplink transmission opportunities the wearable device will not use for uplink transmission. For example, the cellular radio device may omit transmission of measurement data in one or more consecutive uplink resources because of lack of measurement data to transmit. The cellular radio device may also be configured to enter a power-saving mode between the transmissions such that the cellular radio device is woken up and energized upon the measurement data becoming available. Consequently, the cellular radio device may also omit reception of one or more downlink control signals from the access node 110 because of the power-save mode.

Upon detecting the mismatch where there are excessive resources allocated to the terminal device, the cellular radio device or the access node may initiate the reduction of the allocated radio resources in order to improve the efficiency of the cellular communication system. If the process is initiated by the cellular radio device, the process may comprise the exchange of the request and response, as described above in steps 312, 314 with the modification that now the request is for a reduced amount of allocated uplink resources. After the reallocation, the allocated resources may again be matched with the rate at which the measurement data becomes available.

Figure 5:
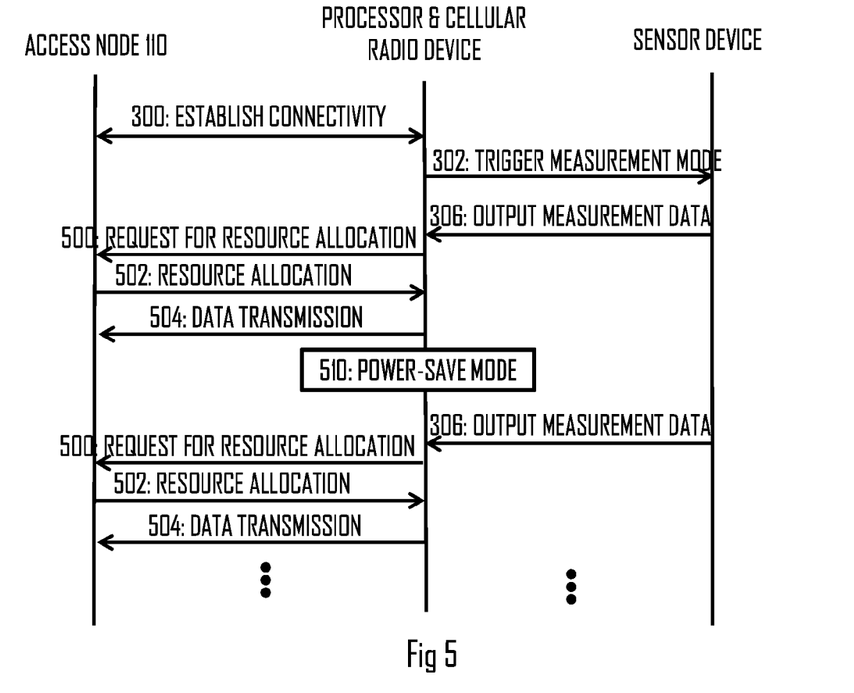
FIG. 5 illustrates an embodiment for transmitting measurement data on a need basis and employing power-saving according to an embodiment of the invention.

Some cellular communication systems enable the terminal device to enter a power-save mode in which the bearer services remain in a stand-by state for fast activation. No radio resources are necessarily allocated to the terminal device in the power-save mode. Modern systems such as the 5G system have been envisaged to support expedited duration in the power-save mode and to provide a fast cellular access whenever the terminal device awakes to perform the uplink transmission. Since the bearer service(s) is/are maintained, the connectivity is maintained even during the power-save mode. FIG. 5 illustrates a process where the terminal device awakes to transmit the measurement data.

Referring to FIG. 5, the steps denoted by the same reference numbers as in FIG. 3 represent substantially similar operations. Upon detecting the measurement data in step 306, the processor may wake up the cellular radio device from the power-save mode to perform the uplink transmission. Upon waking up, the cellular radio device may send a resource allocation request to the access node 110 (step 500). The request may specify the amount of uplink resources requested. Upon receiving the request in step 500, the access node may grant an uplink resource to the cellular radio device and transmit an uplink resource grant message in step 502. Upon receiving the grant, the cellular radio device may perform uplink transmission in the requested resource (step 504). Because the parameters of the connection are maintained during the power-save mode, steps 500 to 504 may be carried out with low latency. Upon transmitting the measurement data, the cellular radio device may again enter the power-save mode 510 and, upon receiving more measurement data, the processor may again wake up the cellular radio device for another uplink transmission (reiteration of steps 306 and 500 to 504).

Figure 6:
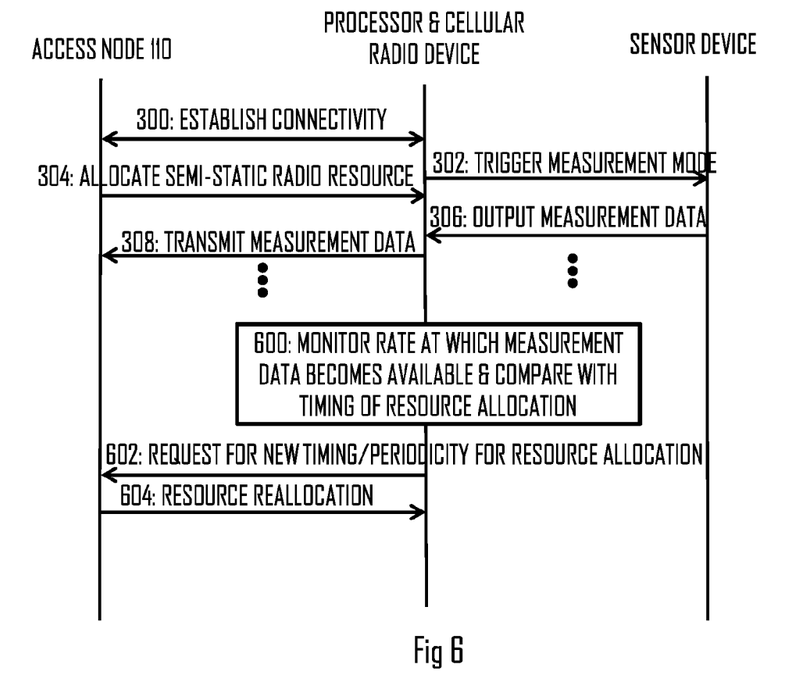
FIG. 6 illustrates a procedure for adapting timing of uplink resources to measurement data availability according to an embodiment of the invention.

As already indicated above, the timing of the uplink resource allocation may be matched with the rate at which the measurement data becomes available. FIG. 6 illustrates a process for matching the timing of the uplink resource allocation with the rate at which the measurement data becomes available. Again, the steps denoted by the same reference numbers as in FIG. 3 represent substantially similar operations. In block 600, the processor may monitor the rate at which the measurement data is received from the sensor device and compares the rate with the currently allocated uplink resources. In particular, step 600 may comprise monitoring timing of the received measurement data and timing of the uplink resources. Upon detecting that the timing of the uplink resource is not matched with the timing of the measurement data, the processor may instruct the cellular radio device to request for the new timing that better matches with the timing of the measurement data. As a response, the cellular radio device may transmit a request for new timing for the resource allocation to the access node in step 602. In step 604, the cellular radio device receives a new resource allocation that complies with the requested timing of the uplink resources. In this manner, the processor may actively keep the uplink resources aligned with the measurement data such that the real-time uplink transmission characteristics of the measurement data may be improved.

The timing monitored in block 600 may comprise a time interval between a timing when the measurement data is entered to the uplink buffer and a timing of the uplink resource subsequent to the entering. Upon detecting that the time interval is higher than a threshold, the processor may request the cellular radio device to request for advancing the uplink resource allocation in step 602. Other parameters of the resource allocation such as the amount of resources and periodicity of the resources may be maintained.

The comparison may comprise comparing periodicity of the measurement data and periodicity of the uplink resource. Upon detecting that the periodicities are mismatched, the processor may request the cellular radio device to request for changing the periodicity of the uplink resource allocation in step 602 to match with the periodicity of the measurement data. Other parameters of the resource allocation such as the amount of resources may be maintained.

Figure 7:
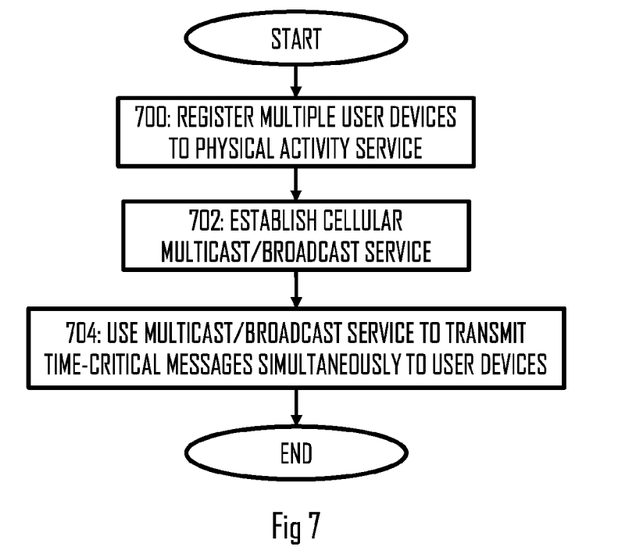
FIG. 7 illustrates an embodiment for providing a physical activity service employing a cellular communication system according to an embodiment of the invention.

FIG. 7 illustrates an embodiment where the server computer utilizes a multicast/broadcast service of the cellular communication system to transmit data to multiple terminal devices (or user devices) of the cellular communication system. Referring to FIG. 7, a method for managing a physical activity service in the server computer 132 comprises in the server computer: registering (block 700) a plurality of user devices to the physical activity service; establishing (block 702) a cellular multicast or a broadcast service for the physical activity service via a network of access nodes of a cellular communication system; and using (block 704) the multicast or the broadcast service to deliver to the plurality of user devices a time-critical message of the physical activity service that shall be received at the plurality of user devices simultaneously.

Figure 8:
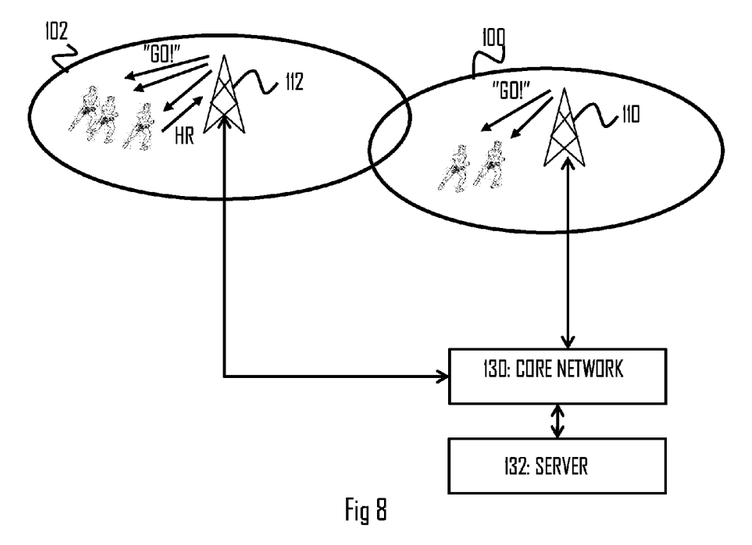
FIG. 8 illustrates utilization of the cellular communication system according to an embodiment of FIG. 7.

FIG. 8 illustrates an embodiment where multiple users have registered to the physical activity service. The service may be related to a race or a competition such as a marathon race. Instead of triggering a start command for the race with a starter pistol, the cellular multicast or a broadcast service may be used to transmit a start command over a radio interface to user devices of the competitors. Since the command is broadcasted or multicast to the user devices, the devices receive the message substantially simultaneously or at least with accuracy acceptable for such a competition. In a similar manner, another time-critical message that triggers launch of a physical activity associated with the physical activity service may be transmitted through the access nodes. An example of such another message is a message of a virtual coaching service where a virtual coach in the form of the server computer 132 instructs multiple users carrying out the same exercise at different, distant geographical locations. The message may instruct the users to start a certain phase in the exercise, specify a target intensity that shall be reached for, or to end a phase in the exercise or the exercise.

In an embodiment, the method of FIGS. 7 and 8 further comprises receiving, at the server computer 132, measurement data of the physical activity service from at least one of the plurality of user devices through an access node 110, 112 of the cellular communication system. Each user may wear the above-described wearable device provided with the cellular communication capability, and uplink messages carrying measurement data may be transmitted by the user devices by using unicast uplink connections. The server computer 132 may thus receive the measurement data individually from each user device and transmit information to the user devices via the multicast/broadcast service.

In an embodiment, a user device may employ its cellular connectivity for at least one other user device and operate as a gateway between the server computer 132 and the other user device. The user device may communicate with the server by using the cellular connectivity and with the other user device via a Bluetooth® link, for example. In the operation as the gateway, the user device may forward data received over the Bluetooth® link to the cellular connection, and forward data received over the cellular connection and addressed to the other device to the Bluetooth® link.

In an embodiment, the multicast or broadcast service is similar to the multimedia broadcast multicast service (MBMS) of LTE networks.

In an embodiment, the server computer 132 uses the multicast or broadcast service to broadcast standings during a competition. In a running competition, the server computer 132 may receive information on locations of the user devices during the competition, determine the standings of associated users on the basis of the received location information, and to transmit the standings through the access nodes 110, 112. The locations may be measured by the user devices by using a satellite positioning system, or the locations may be measured and reported to the server computer by the access nodes 110, 112. Each user device may be associated with an identifier in the physical activity service, and the server computer may transmit the standings in the following form:

TABLE 1

| ID | #1 | #2 | . . . | #N |
|---|---|---|---|---|
| Standing | 4 | 15 | | 1 |

Each user device receiving the message of Table 1 may search for its identifier in the message, extract the standing associated with the identifier, and output an indicator of the standing through a user interface of the user device.

In an embodiment, the server computer is configured to define a geographical or location-based service area for the physical activity service and configure only a subset of access nodes associated with the service area to broadcast or multicast the messages of the physical activity service. In this manner, the server computer 132 may employ the access nodes to perform geocasting for the physical activity service.

Figure 9:
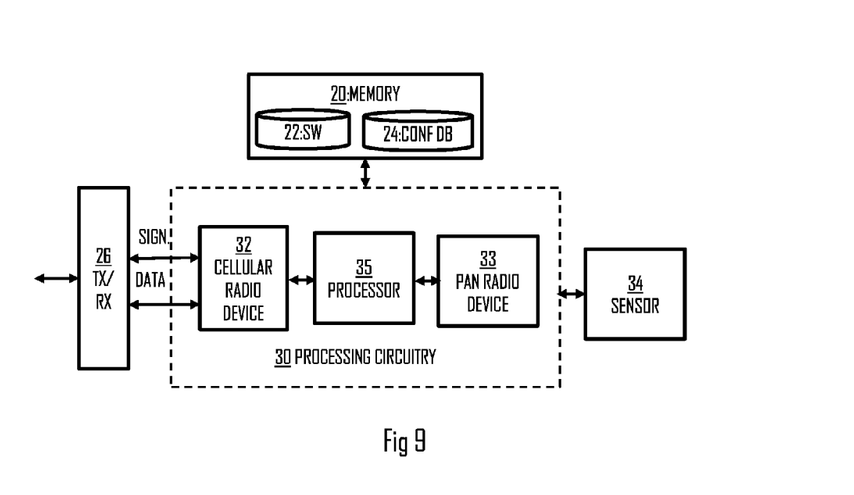
FIGS. 9 and 10 illustrate block diagrams of apparatuses according to some embodiments of the invention.
Figure 10:
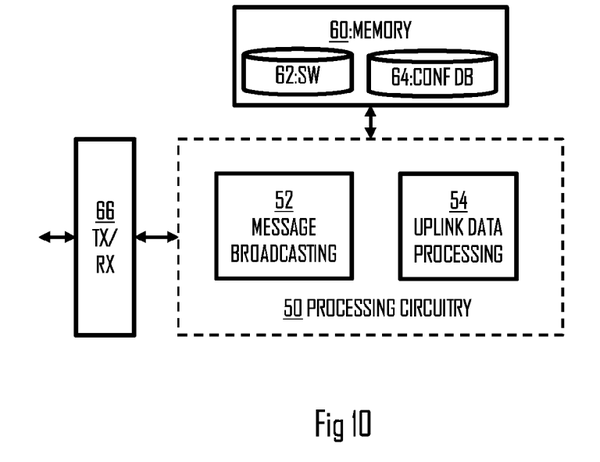

FIGS. 9 and 10 illustrate block diagrams of apparatuses according to some embodiments of the invention. FIG. 9 illustrates the terminal device also called the wearable device and user device in the above description. The apparatus of FIG. 9 may be a wrist device, for example, or the apparatus may be comprised in a wrist device. The apparatus may be, for example, a circuitry or a chipset in the wrist device. The apparatus may be an electronic device comprising electronic circuitries.

Referring to FIG. 9, the apparatus may comprise a processing circuitry 30 such as at least one processor, and at least one memory 20 including a computer program code (software) 22 wherein the at least one memory and the computer program code (software) are configured, with the at least one processor, to cause the apparatus to carry out any one of the embodiments of the wearable device, user device, or the terminal device.

The memory 20 may be implemented using any suitable data storage technology, such as semiconductor based memory devices, flash memory, magnetic memory devices and systems, optical memory devices and systems, fixed memory and removable memory. The memory may comprise a configuration database 24 for storing configuration data for the cellular connectivity and/or the physical activity service.

The apparatus may further comprise a communication interface (TX/RX) 26 comprising hardware and/or software for realizing communication connectivity according to one or more radio communication protocols. The communication interface 26 may provide the apparatus with communication capabilities to communicate in the cellular communication system and/or in another wireless network. The communication interface 26 may comprise standard well-known components such as an amplifier, filter, frequency-converter, (de)modulator, and encoder/decoder circuitries and one or more antennas. The communication interface 26 may comprise radio interface components providing the apparatus with radio communication capability in one or more wireless networks and enable radio communication with one or more access nodes.

The apparatus may further comprise a cellular radio device 32 configured to perform signal processing related to transmission and reception of control message and data messages according to a cellular communication protocol. The cellular radio device 32 may include a cellular radio modem configured to perform at least digital signal processing on a physical layer according to the cellular communication protocol. The cellular radio device may employ the communication interface at least for analogue transmission and reception procedures when communicating with the access nodes of the cellular communication system.

The processing circuitry 30 may further comprise a processor 35 configured to perform the functions of the processor described above. The processor 35 may be configured to manage the radio resource availability such that the measurement data may be streamed to the cellular communication system and to the server computer 132 with a minimal latency.

In an embodiment, the apparatus further comprises at least one of the above-described sensor devices 34.

In an embodiment, the apparatus comprises a radio device 33 configured to establish a personal area network (PAN) radio connection, such as Bluetooth® connection, with one or more sensor devices to receive measurement data.

FIG. 10 illustrates an embodiment of an apparatus suitable for the server computer. The apparatus may be, for example, a circuitry or a chipset in the server computer 132. The apparatus may be the server computer 132. The apparatus may be an electronic device comprising electronic circuitries.

Referring to FIG. 10, the apparatus may comprise a processing circuitry 50 such as at least one processor, and at least one memory 60 including a computer program code (software) 62 wherein the at least one memory and the computer program code (software) are configured, with the at least one processor, to cause the apparatus to carry out any one of the embodiments of the server computer 132.

The memory 60 may be implemented using any suitable data storage technology, such as semiconductor based memory devices, flash memory, magnetic memory devices and systems, optical memory devices and systems, fixed memory and removable memory. The memory may comprise a configuration database 64 for storing configuration data for the physical activity service.

The apparatus may further comprise a communication interface (TX/RX) 66 comprising hardware and/or software for realizing communication connectivity with the cellular communication system and the user devices. The communication interface may comprise a network adapter providing the server computer with communication capability according to Internet Protocol (IP), for example.

The processing circuitry 50 may further comprise a message broadcasting circuitry 52 configured to output messages to be transmitted to the user devices through the broadcast or multicast service of the cellular communication system. The message broadcasting circuitry may monitor for determined events that trigger the transmission of the messages. Such events may time-based events, schedule based events, or exercise program-based events, for example.

The processing circuitry 50 may further comprise an uplink data processing circuitry 54 configured to receive uplink measurement data from at least one user device. In an embodiment described above, the uplink measurement data may indicate timings of physiological events such as heart beats, and the uplink data processing circuitry computes a metric from the received timings, e.g. the heart rate or energy consumption.

In an embodiment, the user devices may add a time stamp to the uplink messages carrying the measurement data. The time stamp may indicate the measurement timing of the physiological event which improves the accuracy of the computation of the uplink data processing circuitry 54. In such embodiments, the processing circuitry 50 may further comprise a clock synchronization circuitry configured to maintain clock synchronization with the user devices.

As used in this application, the term 'circuitry' refers to all of the following: (a) hardware-only circuit implementations, such as implementations in only analog and/or digital circuitry, and (b) combinations of circuits and soft-ware (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chipset (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 2 to 8 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a person of ordinary skill in the art.

Figure 11:
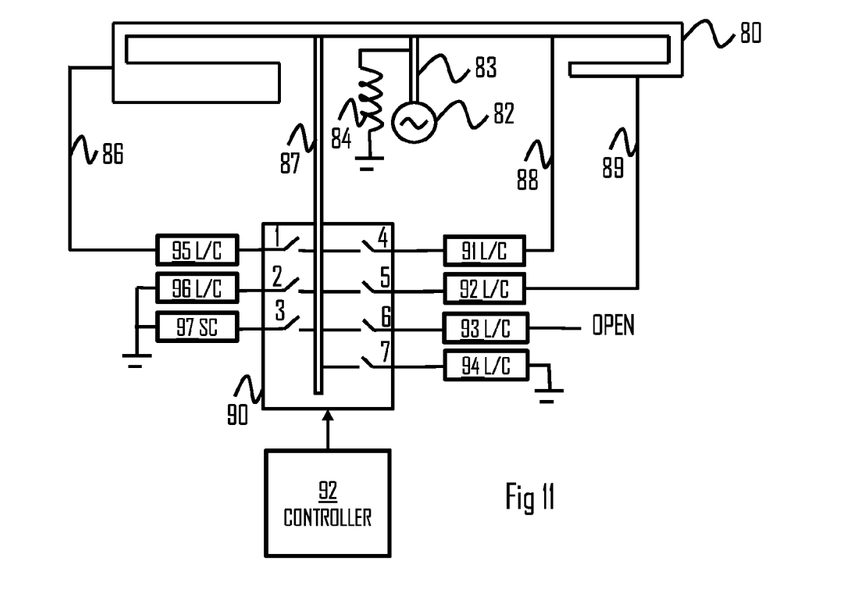
FIG. 11 illustrates an antenna arrangement suitable for a wearable device provided with cellular communication capability.

FIG. 11 illustrates an embodiment of an antenna configuration suitable for the wearable devices 12 provided with the cellular communication capability, although the antenna configuration may be applicable to other devices as well.

FIG. 11 illustrates the embodiments as realized in connection with an inverted F-antenna 80 (IFA). The IFA could be planar to make it planar IFA (PIFA). Regarding basic antenna configurations, FIG. 11 illustrates a signal source 82 configured to provide a signal for transmission, e.g. a signal source providing the uplink messages described above. FIG. 11 further illustrates a tuning element 84 for tuning resonance properties of the IFA 80.

Embodiments of the antenna configuration provide for a switching mechanism to generate a loop antenna from the basic planar or strip-line antenna structure, such as the IFA 80 in FIG. 11.

Referring to FIG. 11, let us describe an antenna structure for a radio device, the antenna structure comprising:

a feed line 83 to receive a radio frequency signal from a signal source 82;

an antenna resonator 80 configured to transform the radio frequency signal into electromagnetic radiation;

a switching assembly 90 comprising a plurality of switches 1 to 7;

a first signal line 87 coupling a first location of the antenna resonator 80 to the switching assembly 90;

at least a second signal line 86, 88, 89 coupling at least a second location of the antenna resonator 80 to the switching assembly and, via at least one switch 1, 4, 5, to the first signal line 87 such that, when the at least one switch 1, 4, 5 is closed, the antenna resonator together with the first signal line and the at least second signal line forms a loop antenna comprising at least one loop.

In an embodiment, the first signal line 87 is fixedly coupled with the antenna resonator 80 and to a plurality of switches 1 to 7 of the switching assembly 90, e.g. to all switches 1 to 7.

In an embodiment, the switches 1 to 7 are controlled by a controller 92 configured to output a control signal to close and/or open the switches 1 to 7 according to a determined criterion.

As illustrated in FIG. 11, the at least second signal line may in fact encompass multiple signal lines 86, 88, 89 attached to different locations of the resonator 80. Each signal line 86, 88, 89 may be coupled to a different switch 1, 4, 5 of the switching assembly. Accordingly, multiple spatially and operationally different loop antenna configurations may be formed by opening and closing the switches 1, 4, 5. In FIG. 11, the signal line 88 is coupled to the resonator 80 on the same plane as the first signal line 87 but on a different location. The signal line 86 is coupled to a plane perpendicular to the plane to which the first signal line 87 is coupled, and the signal line 89 is coupled to a plane parallel to the plane to which the first signal line 87 is coupled. Each coupling locations provide different resonance characteristics to the loop antenna, e.g. different operating frequencies, different bandwidths, different Q values, and/or different impedances.

Some of the switches 1 to 7 may be coupled at first end to the first signal line and at the other end to an impedance circuitry 91 to 96 to provide further tuning options for the antenna structure. Some of the impedance circuitries may be coupled to the ground at the other end such as impedance circuitries 94 and 96, and some of the impedance circuitries may be configured as open circuits such as impedance circuit 93.

Each of the impedance circuitries 91 to 96 may form capacitive, resistive, and/or inductive impedance. Additionally, a short circuit 97 may be coupled to a switch 3 to provide a short circuit to the ground. In an embodiment, at least some of the impedance circuitries 91, 92, 95 coupled to the respective signal lines 88, 89, 86 may be short circuits.

Let us now describe some antenna configurations that may be formed with the arrangement of FIG. 11. A first loop antenna configuration may be formed by closing switch 1 and the loop is formed by the signal lines 86, 87 and the impedance circuitry 95. The first loop antenna configuration may be tuned by closing any one or more of the switches 93, 94, 96, 97 according to the desired operational characteristics of the first loop antenna configuration.

A second loop antenna configuration may be formed by closing switch 4 and the loop is formed by the signal lines 87, 88, and the impedance circuitry 91. The second loop antenna configuration may be tuned by closing any one or more of the switches 93, 94, 96, 97 according to the desired operational characteristics of the second loop antenna configuration.

A third loop antenna configuration may be formed by closing switch 5 and the loop is formed by the signal lines 87, 89 and the impedance circuitry 92. The third loop antenna configuration may be tuned by closing any one or more of the switches 93, 94, 96, 97 according to the desired operational characteristics of the third loop antenna configuration.

A fourth loop antenna configuration may be formed by closing switches 1 and 4 to generate three antenna loops. A first loop is formed by the signal lines 86, 87 and the impedance circuitry 95, a second loop is formed by the signal lines 87, 88, and the impedance circuitry 91, and a third loop is formed by the signal lines 86, 88, and the impedance circuitries 91, 95. The fourth loop antenna configuration may be tuned by closing any one or more of the switches 93, 94, 96, 97 according to the desired operational characteristics of the fourth loop antenna configuration.

A fifth loop antenna configuration may be formed by closing switches 1 and 5 to generate three antenna loops. A first loop is formed by the signal lines 86, 87 and the impedance circuitry 95, a second loop is formed by the signal lines 87, 89, and the impedance circuitry 92, and a third loop is formed by the signal lines 86, 89, and the impedance circuitries 92, 95. The fifth loop antenna configuration may be tuned by closing any one or more of the switches 93, 94, 96, 97 according to the desired operational characteristics of the fifth loop fourth loop antenna configuration.

A sixth loop antenna configuration may be formed by closing switches 4 and 5 to generate three antenna loops. A first loop is formed by the signal lines 87, 88 and the impedance circuitry 91, a second loop is formed by the signal lines 87, 89, and the impedance circuitry 92, and a third loop is formed by the signal lines 88, 89, and the impedance circuitries 91, 92. The sixth loop antenna configuration may be tuned by closing any one or more of the switches 93, 94, 96, 97 according to the desired operational characteristics of the sixth loop antenna configuration.

A seventh loop antenna configuration may be formed by closing switches 1, 4, and 5 to generate six antenna loops. A first loop is formed by the signal lines 86, 87 and the impedance circuitry 95, a second loop is formed by signal lines 86, 88, and the impedance circuitries 91, 95, a third loop is formed by the signal lines 86, 89, and the impedance circuitries 92, 95, a fourth loop is formed by the signal lines 87, 88, and the impedance circuitry 91, a fifth loop is formed by the signal lines 86, 89, and the impedance circuitry 92, and a sixth loop is formed by the signal lines 88, 89, and the impedance circuitries 91, 92. The seventh loop antenna configuration may be tuned by closing any one or more of the switches 93, 94, 96, 97 according to the desired operational characteristics of the seventh loop antenna configuration.

The controller 92 may have access to a mapping table defining different antenna configurations comprising at least some of the above-described loop antenna configurations and, additionally, a further antenna configuration where the antenna operates according to its basic configuration such as the IFA. The mapping table may associate each transmission mode with an antenna configuration, and the controller 92 may select the antenna configuration upon receiving an indication of the transmission mode. The transmission mode may be defined by frequency band properties such as an operating band and/or bandwidth, a communication protocol such as the cellular communication protocol or the Bluetooth® communication protocol, etc. In this manner, the basic antenna resonator 80 may be converted into various loop antenna configurations, thus providing flexibility. Such an adaptable antenna structure may also reduce the physical size needed which is an advantage in wearable devices 12.

In an embodiment, the switching assembly 90 or another switching assembly may be used to couple two or more separate antennas into a single antenna assembly. Each antenna may have a dedicated signal feed, although another switching mechanism may selectively disconnect at least one of the feeds while maintaining at least one antenna feed in the antenna assembly. The switching assembly may be used to form a loop antenna from two IFA antennas, for example. By connecting the antennas from different locations to the switching assembly and through appropriate closing and opening of the switches, various antenna configurations may be created, thus improving flexibility of the antenna configuration to configure the antenna assembly with different radiation properties, e.g. operation on multiple frequency bands by using the same antenna elements. It would be advantageous in small-sized devices with multiple radio heads, for example. Such devices may comprise wrist computers or small-sized sensor devices, for example.

It will be obvious to a person skilled in the art that, as the technology advances, the inventive concept can be implemented in various ways. The invention and its embodiments are not limited to the examples described above but may vary within the scope of the claims.

The invention claimed is:

1. A method for operating cellular connectivity in a wearable device, the method comprising, as performed by the wearable device:
   configuring a sensor device to measure physical activity of a user and to output measurement data representing the measured physical activity;
   establishing, by using a cellular radio device comprised in the wearable device, cellular connectivity with an access node of a cellular communication system;
   receiving, by using the cellular radio device, a cellular uplink resource allocation from the access node for uplink transmission of data; and
   adjusting utilization of cellular uplink resources allocated to the cellular radio device according to a rate at which said measurement data from the sensor device becomes available for uplink transmission in the wearable device, wherein said adjusting comprises:
   detecting a mismatch between the cellular uplink resources allocated to the cellular radio device and the rate at which said measurement data from the sensor device becomes available for uplink transmission in the wearable device; and
   in response to said detecting, using the cellular radio device to request for reallocation of the cellular uplink resources from the access node.

2. The method of claim 1, wherein said adjusting comprises:
   transmitting, by using the cellular radio device, a request message to the access node to adjust uplink resource allocation of the cellular radio device; and
   receiving, by the cellular radio device, a response to the request message from the access node.

3. The method of claim 2, wherein the wearable device requests with a request message for adjustment to a timing of the resource allocation such that the timing of the resource allocation is matched with the rate at which said measurement data from the sensor device becomes available for uplink transmission in the wearable device.

4. The method of claim 2, wherein the wearable device requests with the request message for adjustment to a periodicity of the resource allocation such that the periodicity of the resource allocation is matched with the rate at which said measurement data from the sensor device becomes available for uplink transmission in the wearable device.

5. The method of claim 1, wherein said adjusting comprises omitting uplink transmission in at least one uplink resource allocated to the cellular radio device when there exists no measurement data to transmit.

6. The method of claim 1, wherein the sensor device comprises a heart activity sensor and the measurement data is heart activity measurement data representing heart activity of the user, wherein the heart activity measurement data becomes available for uplink transmission upon the sensor device detecting a heart impulse, and wherein the adjusting comprises matching an uplink transmission rate of the cellular radio device with a rate of detected heart impulses.

7. The method of claim 1, wherein the detected mismatch is a lack of sufficient uplink resources for uplink transmission of the measurement data, and wherein the request indicates a need for additional uplink resources.

8. The method of claim 1, wherein the detected mismatch is an excess in allocated uplink resources, and wherein the request indicates a release of at least some of the allocated uplink resources.

9. The method of claim 1, wherein the mismatch is in periodicity of the allocated uplink resources with respect to a periodicity of the measurement data, and wherein the request indicates a need to change the periodicity of the allocated uplink resources.

10. An apparatus for operating cellular connectivity in a wearable device, the apparatus comprising:
    a cellular radio device configured to communication in a cellular communication system; and
    a processing system arranged to configure a sensor device to measure physical activity of a user and to output measurement data representing the measured physical activity, to establish, by using the cellular radio device, cellular connectivity with an access node of the cellular communication system, to receive, by using the cellular radio device, a cellular uplink resource allocation from the access node for uplink transmission of data, and to adjust utilization of cellular uplink resources allocated to the cellular radio device according to a rate at which said measurement data from the sensor device becomes available for uplink transmission, wherein the processing system is configured to perform said adjusting by performing operations comprising:

detecting a mismatch between the cellular uplink resources allocated to the cellular radio device and the rate at which said measurement data from the sensor device becomes available for uplink transmission in the wearable device; and in response to said detecting, using the cellular radio device to request for reallocation of the cellular uplink resources from the access node.

11. The apparatus of claim 10, wherein the processing system is arranged to adjust the utilization of the cellular uplink resources by transmitting, by using the cellular radio device, a request message to the access node to adjust uplink resource allocation of the cellular radio device and by receiving, through the cellular radio device, a response to the request message from the access node.

12. The apparatus of claim 11, wherein the processing system is configured to use the cellular radio device to request, with a request message, for adjustment to a timing of the resource allocation such that the timing of the resource allocation is matched with the rate at which said measurement data from the sensor device becomes available for uplink transmission.

13. The apparatus of claim 11, wherein the processing system is configured to use the cellular radio device to request with the request message for adjustment to a periodicity of the resource allocation such that the periodicity of the resource allocation is matched with the rate at which said measurement data from the sensor device becomes available for uplink transmission.

14. The apparatus of claim 10, wherein the processing system is arranged to adjust the utilization of the cellular uplink resources by configuring the cellular radio device to omit uplink transmission in at least one uplink resource allocated to the cellular radio device when there exists no measurement data to transmit.

15. The apparatus of claim 10, wherein the sensor device comprises a heart activity sensor and the measurement data is heart activity measurement data representing heart activity of the user, wherein the heart activity measurement data becomes available for uplink transmission upon the sensor device detecting a heart impulse, and wherein the processing system is arranged to adjust the utilization of the cellular uplink resources by matching an uplink transmission rate of the cellular radio device with a rate of detected heart impulses.

16. The apparatus of claim 10, wherein the detected mismatch is a lack of sufficient uplink resources for uplink transmission of the measurement data, and wherein the request indicates a need for additional uplink resources.

17. The apparatus of claim 10, wherein the detected mismatch is an excess in allocated uplink resources, and wherein the request indicates a release of at least some of the allocated uplink resources.

18. The apparatus of claim 10, wherein the mismatch is in periodicity of the allocated uplink resources with respect to a periodicity of the measurement data, and wherein the request indicates a need to change the periodicity of the allocated uplink resources.

19. A computer program product embodied on a non-transitory distribution medium readable by a computer and comprising program instructions which, when executed by the computer, result in execution of a computer process in a wearable device, the computer process comprising:

configuring a sensor device to measure physical activity of a user and to output measurement data representing the measured physical activity;

establishing, by using a cellular radio device comprised in the wearable device, cellular connectivity with an access node of a cellular communication system;

receiving, by using the cellular radio device, a cellular uplink resource allocation from the access node for uplink transmission of data; and adjusting utilization of cellular uplink resources allocated to the cellular radio device according to a rate at which said measurement data from the sensor device becomes available for uplink transmission in the wearable device, wherein said adjusting comprises:

detecting a mismatch between the cellular uplink resources allocated to the cellular radio device and the rate at which said measurement data from the sensor device becomes available for uplink transmission in the wearable device; and in response to said detecting, using the cellular radio device to request for reallocation of the cellular uplink resources from the access node.

\* \* \* \* \*